United States Patent [19]

Bertozzi

[11] Patent Number: 5,115,459
[45] Date of Patent: May 19, 1992

[54] EXPLOSIVES DETECTION USING RESONANCE FLUORESCENCE OF BREMSSTRAHLUNG RADIATION

[75] Inventor: William Bertozzi, Lexington, Mass.

[73] Assignee: Massachusetts Institute of Technology, Cambridge, Mass.

[21] Appl. No.: 620,266

[22] Filed: Nov. 30, 1990

Related U.S. Application Data

[63] Continuation-in-part of Ser. No. 567,970, Aug. 15, 1990.

[51] Int. Cl.$^5$ .......................................... G01N 23/201
[52] U.S. Cl. ......................................... 378/88; 378/57; 378/3; 378/87
[58] Field of Search .................. 378/3, 86, 87, 88, 89, 378/57

[56] References Cited

U.S. PATENT DOCUMENTS

| | | | |
|---|---|---|---|
| 4,864,142 | 9/1989 | Gomberg | 378/57 |
| 4,941,162 | 7/1990 | Vartsky et al. | 378/3 |

OTHER PUBLICATIONS

"Nuclear and X-ray Technologies for Airport Security", An expanded version of a talk at the MIT Symposium, Lee Grodzins, Apr. 17, 1990.

"Nuclear Techniques for Finding Chemical Explosives in Airport Luggage", Lee Gordzins, Int. Conf. on the Application of Accelerators, Nov. 1990.

"Nuclear-Based Methods for Detecting Explosives", L. Gordzins, Testimony before the Sub-Committee on Government Activities and Transportation House Government Operations Committee, Sep. 26, 1989.

"Resonance-Fluorescence Studies. I. $^{45}$Sc, $^{69}$Ga, and $^{71}$Ga", Raymond G. Arnold et al., Physical Review C, 7, No. 4, pp. 1490-1500, Apr. 1973.

"Resonance-Fluorescence Studies. II. $^{121}$Sb and $^{123}$Sb", Edward C. Booth et al., Physical Review C, 7, No. 4, pp. 1500-1509, Apr. 1973.

"Resonance Fluorescence of Giant Magnetic Dipole States in $^{24}$Mg", Berg et al., Physical Review C, 11, No. 5, pp. 1851-1853, May 1975.

"Resonance Fluorescence of $^{23}$Na Above 3 MeV*", D. L. Friesel et al., Physical Review C, 6, No. 3, pp. 846-850, Sep. 1972.

"Gamma-Ray Excitation of the 1.51-Mev Level in $C^{12*}$", E. L. Garwin, Physical Review, 114, No. 1, pp. 143-154, Apr. 1959.

"Resonant Scattering of Gamma Rays from Nuclear Levels with a Linear Accelerator", F. D. Seward, Physical Review, 125, No. 1, pp. 335-340, Jan. 1962.

"Width of the 2.186-MeV—Level in $Nd^{144}$", F. R. Metzger, Physical Review, 187, No. 4, pp. 1700-1704, Nov. 1969.

(List continued on next page.)

Primary Examiner—Craig E. Church
Attorney, Agent, or Firm—Choate, Hall & Stewart

[57] ABSTRACT

A technique for detecting explosives using resonance fluorescence of bremsstrahlung radiation is disclosed. The method is particularly attractive as a way to detect bombs at airports and other transportation terminals. According to the invention, bremsstrahlung radiation is made incident on a target (e.g., a piece of luggage) to resonantly excite the atoms of the target. In one embodiment, the energies of the photons scattered directly from the target are detected and measured. These energies are characteristic of the nuclear species excited in the target, and thus the concentrations of these elements in the target can be determined. A high concentration of nitrogen and oxygen with a low concentration of carbon indicates practically without fail an explosive material. In another embodiment, the energies of photons resonantly scattered from reference scatterers composed substantially of nuclear species of interest and located downstream from the target are detected and measured. The abundance of photons of energies corresponding to nuclear species of interest detected in this embodiment is inversely related to the abundance of the species in the target.

42 Claims, 4 Drawing Sheets

OTHER PUBLICATIONS

"Electric Dipole Transitions from the 2.6-MeV Suptuplet in $Bi^{209}$", F. R. Metzger, Physical Review, 187, No. 4, pp. 1680–1682, Nov. 1969.

"Radiative Width of the 2.31-MeV Level in $^{14}N$", V. K. Rassmussen et al., Physical Review C, 12, No. 2, pp. 706–707, Aug. 1975.

"Gamma-Ray Widths in $C^{13}$, $Li^6$, and $P^{31}$", V. K. Rasmussen et al., Physical Review, 183, No. 4, Jul. 1969.

"A Facility for Resonance-Fluorescence Experiments Using an Electron Linac", N. Shikazono et al., Nuclear Inst. & Methods, 92, pp. 349–357, 1971.

"Widths of the 6.92 and 7.12 MeV Levels in $^{16}O$ and the Influence of the Effective Temperature", R. Moreh et al., Physical Review C, 31, No. 6, pp. 2314–2316, Jun. 1985.

"Resonant Scattering of Bremsstrahlung by $^{90}Zr$", F. R. Metzger, Physical Review C, 9, No. 4, pp. 1525–1528, Apr. 1974.

EXPLOSIVES DETECTION USING RESONANCE FLUORESCENCE OF BREMSSTRAHLUNG RADIATION

This application is a continuation-in-part of U.S. application Ser. No. 567,970, filed Aug. 15, 1990.

BACKGROUND OF THE INVENTION

This invention relates to explosives detection at, for example, airports and other transportation terminals, and more particularly, to a method and apparatus for detecting explosives and other materials using resonance fluorescence of bremsstrahlung radiation.

Most explosive materials have relatively high nitrogen and oxygen concentrations. Some common materials also have high nitrogen or high oxygen concentrations; however, almost no common materials have both the high nitrogen and high oxygen concentrations of explosives. Thus, the detection of most explosives would be greatly facilitated if the abundances of nitrogen and oxygen in a sample could be determined. Practically a 100% certainty of identification could be achieved for most kinds of explosives, including plastic explosives, TNT, dynamite, ammonium nitrate, and nitroglycerin. Detection of other elements, such as chlorine, could further decrease the uncertainty of identification for an even wider range of explosives.

There are many requirements that bomb detecting apparatus at airports must meet. First, the measurements must be reliable. Also, the searches must be non-invasive and non-destructive. Since the articles to be examined are sizeable, the use of penetrating radiation is attractive; however, the radiation must not leave the baggage radioactive. Radiation should be easy to shield so as to make the environment safe for people without the need for bulky and expensive walls. The capability to image a target is often important in bomb detection. In addition, measurements should not take more than several seconds per piece of baggage. Finally, as there is a need for thousands of these facilities, with several at most airports, cost is an important consideration.

SUMMARY OF THE INVENTION

The method of the present invention exploits the resonant scattering of photons by nuclei. It involves resonantly exciting the nuclei of a target, a suitcase for example, with a bremsstrahlung photon beam incident on the target. In one embodiment, the subject of copending U.S. application Ser. No. 567,970, the energies of the photons scattered directly from the target are measured. The energies of the scattered photons are characteristic of the spacings between the quantized energy state of each nuclear species comprising the target. For example, oxygen has a discrete energy level at 6.92 MeV of excitation characterized by even parity and two units of angular momentum. A bremsstrahlung beam incident on a target with oxygen will excite some of the nuclei to this state. The state will subsequently decay with a lifetime of about $6.8 \times 10^{-15}$ seconds by emitting a photon with an energy of 6.92 Mev.

Apparatus according to this embodiment of the present invention includes a source of bremsstrahlung radiation comprising an electron source producing electrons incident on a bremsstrahlung target to produce bremsstrahlung radiation, a beam stopper to absorb the electrons, a filter to absorb the low energy end of the bremsstrahlung spectrum, and an aperture to collimate the bremsstrahlung radiation. Appropriate shielding surrounds the bremsstrahlung source. The apparatus further includes detecting apparatus to capture, measure, count, and record the energies of photons scattered from a target. This detecting apparatus also employs appropriate filtering and shielding. A beam dump absorbs the photons transmitted through the target. Shielding surrounds the entire set-up to protect the public from photons and neutrons. A computing apparatus accepts signals from the detecting apparatus and uses this data to distinguish a "suspicious" suitcase from a "normal" one.

The angular distribution of the scattered photons is very broad, and, for the purposes of qualitatively describing the present application, may be considered almost isotropic. Therefore, detectors at almost any angle will detect the scattered photons. The detected intensity, normalized by the incident beam intensity and detector efficiency, will yield an accurate measure of the abundances of various elements. The measurement can be achieved in several seconds with a reasonably simple set of analysis algorithms.

The bremsstrahlung beam can be collimated to a small spot or a thin strip, for example. By sweeping the collimated beam, one can image the target. Imaging can also be achieved by flooding the target with bremsstrahlung radiation and using directional detectors. A combination of the two techniques is also possible.

An alternate detecting scheme is disclosed in the present application which involves making the photons that are transmitted through the target also be incident on one or more reference resonance scatterers located downstream from the target. Each reference scatterer is composed substantially of one or more nuclear species of interest and is associated with a detecting apparatus to detect photons scattered from the reference scatterer. If the target contains an abundance of a nuclear species of interest, photons of energies corresponding to that nuclear species will be resonantly absorbed and will not become incident on the reference scatterers. Thus the signal recorded by the detecting apparatus associated with a reference scatterer comprising that nuclear species will be diminished when the target is placed in the path of the bremsstrahlung beam. This detecting scheme is compatible with, and may be used in combination with, detecting the photons scattered directly from the target.

DESCRIPTION OF THE PREFERRED EMBODIMENT

Figure 1:
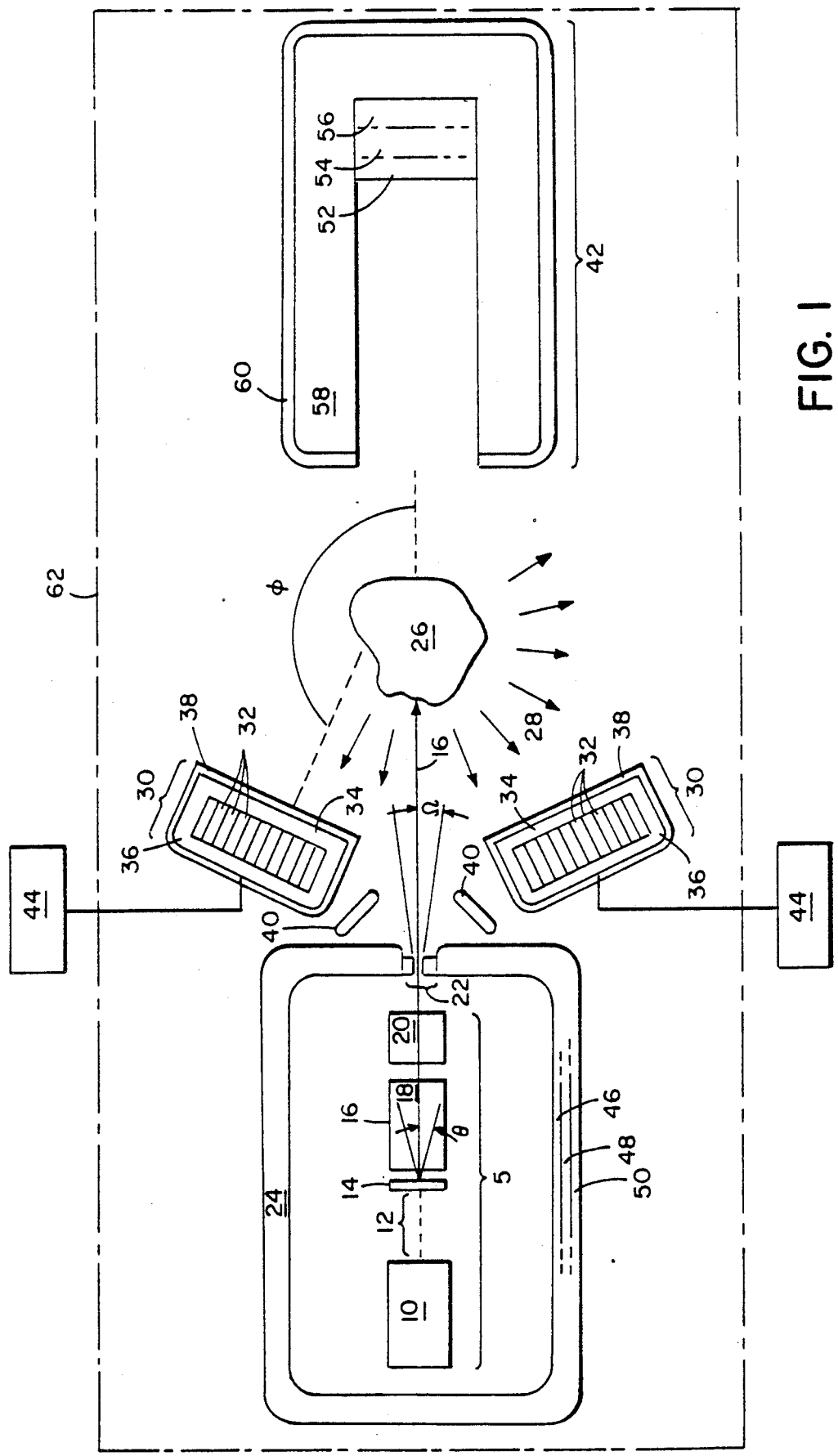
FIG. 1 is a schematic diagram of one embodiment of the explosives detector of the present invention.

One embodiment of the present invention which was disclosed in copending U.S. application Ser. No. 567,970, and is particularly appropriate for detecting explosives in suitcases, is illustrated schematically in FIG. 1. As shown, an electron source 10 provides a beam of electrons 12 incident on a bremsstrahlung target 14 to generate a bremsstrahlung photon beam 16. The bremsstrahlung target 14 is preferably followed by a beam stopper 18 to stop the electrons 12. A filter 20 preferably follows the beam stopper 18 to filter out low energy photons from the bremsstrahlung beam 16. An aperture 22 is employed to collimate the bremsstrahlung beam 16. Shielding 24 encloses the bremsstrahlung-generating apparatus 5. A target 26 (a piece of luggage, for example) is placed in the path of the bremsstrahlung beam 16 (by a conveyor belt, for example). The incident beam 16 resonantly excites the atoms of the target, and photons 28 are scattered from the target 26. The energies of the scattered photons 28 are characteristic of the spacings between the quantized energy states of the nuclei of the target 26. Detecting apparatus 30, including an array of detector 32, captures, measures, counts, and records the energies of the photons 28 scattered in a given direction or directions. The detecting apparatus 30 preferably further includes a filter 34 over the face of each detector to absorb low energy photons, and shielding 36 and 38. As scattering and diffraction from the collimating aperture 22 could lead to a significant amount of photons directed toward the detecting apparatus 30, a shadow shield 40 between the aperture 22 and the detecting apparatus 30 is suggested. A beam dump 42 is provided to absorb the energy of the beam 16 not absorbed in the target 26. Shielding 62 encloses the entire device while allowing convenient means for the entry and exit of targets. Data from the detecting apparatus 30 is sent to a computing apparatus 44 which analyzes the data and determines the abundances of particular elements. The computing apparatus is preferably adapted to compare the data for each piece of luggage to profiles of "normal" luggage to determine if a piece of luggage should be considered "suspicious".

The electron source 10 is any accelerator capable of producing a beam of electrons 12 at the required energies and with the required intensity and duty ratio. Among the suitable accelerators are linear accelerators, electrostatic accelerators, microtrons, and betatrons, all of which are commercially available. The electron energies required in the present invention are on the order of 10 MeV. It is preferable that energies not exceed about 10 MeV so that radioactivity and neutron production does not occur. The beam intensity required is on the order of at least 10 µA; however, an accelerator capable of producing a beam of intensity in excess of 100 µA is preferred. Duty ratio is important and more than one percent is very desireable. Cost and size are also important considerations.

The bremsstrahlung target 14 is a suitable thickness of any material with a high atomic number of nuclear charge (high Z) and a high melting and boiling point, such as tungsten, tantalum, thorium, or uranium. As an electron in the beam passes through the bremsstrahlung target, it produces the electromagnetic radiation called bremsstrahlung radiation which consists of quanta of photons. The spectrum of energies of these photons is continuous, spanning from very low energies to a maximum energy equal to the kinetic energy of the electrons in the beam. This radiation goes by various terms depending on the target and filtering process employed. The terms include thin target bremsstrahlung, thick target bremsstrahlung, filtered bremsstrahlung, and others. Here, the term bremsstrahlung is used to encompass all varieties of bremsstrahlung radiation.

A bremsstrahlung target comprising a thickness of tungsten about the order of 1 gram/cm² is appropriate for most embodiments of the target invention. A substantially thinner target would not provide a sufficient intensity of high energy photons. A substantially thicker target would be self-absorptive of the high energy photons.

The half-angle $\theta_n$ of the natural angular spread of the bremsstrahlung beam for target thickness approaching zero is $\theta_n \approx m_o C^2/E_o$, where $\theta$ is in radians and is measured relative to the direction of the incident electron beam, $m_o$ is the mass of the electrons, c is the speed of light, and $E_o$ is the energy of the electrons. For 10 MeV electrons, $\theta_n \approx 2.9°$. This natural collimation is not completely useful in the present application, however, since the intensity of photons produced with a target thin enough to provide this natural collimation does not meet the present requirements without the use of much higher electron beam currents. An increased current would require a considerably more expensive accelerator and shielding apparatus.

Energy is also absorbed from the electrons in the beam by atomic ionization and by the excitation of the atomic electrons in the bremsstrahlung target. In the process of interacting with the atoms of the target, the electrons often suffer a deflection. The cumulative effect of these deflections is to increase the angular spread of the bremsstrahlung beam. The rms half-angle $\theta$ of the angular spread can be estimated as $$\theta \approx \frac{20}{P\beta} \sqrt{T},$$

where $\theta$ is in radians, P is the momentum of the electrons in MeV/c, $\beta$ is the velocity of the electrons in units of the speed of light (and can be taken to be about 1 for this example), and T is the thickness of the bremsstrahlung target in radiation lengths that the electrons have traversed. As an example, 1.0 gram/cm² of tungsten is about 0.15 radiation lengths and $\theta$ is therefore about 0.77 radians or 45 degrees for a 10 MeV electron beam. Small angles of natural angular spread are therefore only achieved when a very thin bremsstrahlung target is used and overall efficiency for converting the electron energy into photons is comprised. Collimating the radiation with an aperture allows almost any beam shape and angular size approaching that produced by the scattering.

The beam stopper 18 follows the bremsstrahlung target. The beam stopper is preferably a low Z material, such as carbon, of a thickness sufficient to absorb the remaining energy of the electrons 12 from the electron source 10. This low Z material will not generate bremsstrahlung radiation with the same efficiency as the bremsstrahlung target 14, but will be heavily ionizing and therefore will stop the electrons. The thickness of carbon required to stop substantially all the electrons in a 10 MeV beam is about 5.5 gram/cm².

It is not advised to simply extend the thickness of the bremsstrahlung target 14 to act as the stopper, because a substantial increase in its thickness would be required to perform this function and its high Z would attenuate more of the useful high energy photons than the stopper 18 of the lighter material. For example, a thickness of 8 gram/cm² of tungsten would be required to stop substantially all electrons of a 10 MeV beam.

It is possible to deflect the electron beam with the use of magnets so that the stopper 18 need not be placed in the line of the bremsstrahlung beam 16. However, since a stopper of low Z material will not substantially affect the bremsstrahlung radiation at the energy levels of interest, this scheme introduces unnecessary complication and expense. On the other hand, the use of a magnet to deflect the electron beam by modest amounts before its strikes the bremsstrahlung target, in order to sweep the resultant direction of the bremsstrahlung beam produced by the bremsstrahlung target, is a possible and useful embodiment for the purposes of imaging.

A filter 20 preferably follows the beam stopper 18. The filter is preferably a low Z material of a thickness sufficient to absorb the low energy end of the bremsstrahlung spectrum preferentially over the high energy end, where the nuclear states of interest lie. The low energy photons in most embodiments of the present invention are those in the region of about 2 MeV or less. A suitable material for this filter is a material with atomic number in the range of carbon to iron. The filter may also be made using a combination of suitable materials. The filter can be tuned to optimize its filtering performance over a desired energy range by selecting the atomic number of the filter material or materials and the thickness of the filter.

An indicated above, it is not practical to rely only on the natural collimation of the bremsstrahlung radiation, since beam intensity is sacrificed by the use of a very thin bremsstrahlung target. Therefore, the aperture 22 is required to produce a collimated beam. The aperture is preferably graded to result in a well-defined beam with little halo. It is advantageous to make the aperture rapidly adjustable to permit quick changes in the beam collimation. Preferred aperture geometries are discussed below in conjunction with imaging techniques.

The shielding 24 includes a first layer 46 of a high Z material, such as bismuth, lead, or iron, of sufficient thickness to absorb substantially all of the energy of the electrons and of the photons.

The first layer of shielding 46 and the collimating aperture 22 could be a prolific source of neutrons from the so-called Giant Electric Dipole resonance in heavier nuclei. These neutrons must be shielded from the detectors so as not to produce too much background from neutron induced reactions. A second layer of shielding 48 is therefore required to substantially absorb the neutrons produced by the bremsstrahlung radiation. This second layer is preferably a hydrogenous material loaded with boron or lithium to preferentially capture the neutrons so that no high energy photons are emitted. Even at 10 MeV, substantial neutron shielding is required. At higher energies, this problem will be much more serious. This loaded hydrogenous material might also be required to cover the exit port of the collimating aperture.

A final layer of shielding 50 of a high Z material such as bismuth, lead, or iron, is required to capture photons generated by neutron capture in the second layer 48 and the outer regions of the first layer 46.

The cross section for the absorption of the photons of the bremsstrahlung beam 16 by the nuclei of the target 26 with ground state spin equal to zero, assuming only photon decay to the ground state (and not proton and other kinds of decay) is involved, is given by $$\frac{d\sigma}{d\epsilon} = \frac{\lambda^2 \Gamma^2 G}{4\pi\left((\epsilon - \epsilon_0)^2 + \left(\frac{\Gamma}{2}\right)^2\right)}$$

where $\lambda$ is the photon wavelength, $\epsilon$ is the photon energy, $\epsilon_0$ is the energy of the state, $\Gamma$ is the full width of the state, and G is a statistical factor equal to $2l+1$. In this last expression, l is the multipolarity of the transition. For nuclei with ground states of spin equal to zero, l is also the spin of the excited state. This cross section has the usual resonance behavior. The peak value of this cross section occurs when $\epsilon = \epsilon_0$ and has the value $\lambda^2(2l+1)/\pi$. The integrated cross section which is of interest for counting rate estimates is given by $\sigma = \lambda^2 \Gamma(2l+1)/\pi$; that is, the peak value of the cross section multiplied by the width $\Gamma$. If other modes of decay are possible, the ground state strength is attenuated. If the ground state spin is different from zero, the formula, although not precise, is still useful for estimating the approximate cross sections.

The nuclear states of interest in the present invention are states that have a width $\Gamma$ that is mostly due to photon decay. Cascades via intermediate states that produce photon energies that are sufficiently high so that they can be detected above background are acceptable. The widths of these states of interest are very small. For the decay of the 6.92 MeV state in oxygen to the ground state, $\Gamma$ is on the order of 1/10 eV. However, the cross sections are large in the peak because $\lambda$ is large. A value of about 200 barns is expected for the 6.92 MeV state in oxygen. This means that most of the photons in the bremsstrahlung spectrum that lie within the resonance peak would be absorbed by a thickness of material that has about 1/10 of a gram of oxygen per cm². The same would be true for nitrogen and carbon, or any other material of interest.

It is important to note that the line widths are made wider by the thermal motion of the molecules, and the technique will not suffer any significant loss of penetration depth because of the large peak cross sections. Unlike the situation where one is scattering a narrow line of photons from a resonance, the thermal broadening of the peak does not cause a loss of sensitivity. In the bremsstrahlung spectrum there are always photons to scatter at whatever energy the resonance is shifted to by thermal molecular or atomic motion.

Nitrogen states of particular relevance to the preferred embodiment of the present invention include:
  the 4.92 MeV 0− state which decays to the 1− ground state with a width of 0.084 eV.
  the 7.03 MeV 2+ state which decays to the 1+ ground state with a width of 0.078 eV.

Oxygen states of particular relevance to the preferred embodiment of the present invention include:
  the 6.92 MeV 2+ state which decays to the 0³⁰ ground state with a width of 0.097 eV.
  the 7.12 MeV 1− state which decays to the 0+ ground state with a width of 0.055 eV.

A carbon state of particular relevance to the preferred embodiment of the present invention is:
  the 4.44 MeV 2+ state which decays to the 0+ ground state with a width of 0.011 eV.

Another oxygen state of interest in the 12.53 MeV 2− state which: decays to a 6.13 MeV 3− state producing a 6.40 MeV photon and a 6.13 MeV photon with a width of 2.1 eV; decays to a 7.12 MeV 1− state producing a 5.41 MeV photon and a 7.12 MeV photon with a width of 0.5 eV; and decays to a 8.87 MeV 2− state producing a 3.66 MeV photon, along with a 1.74 MeV photon and a 6.13 MeV photon in cascade most of the time, with a width of 0.9 eV. Another carbon state of interest is the 12.71 MeV 1+ state which: decays to the 0+ ground state with a width of 0.35 eV; and decays to the 4.44 MeV 2+ state producing a 8.27 MeV photon and a 4.44 MeV photon with a width of 0.053 eV. The total widths of the 12.53 MeV state in oxygen and the 12.71 MeV state in carbon are 97 eV and 18 Ev respectively. These states decay preferentially by proton and/or alpha emission and the photon intensities will be considerably reduced. Thus, these states are not a part of a preferred embodiment because of their low intensity and high energy.

The 15.11 MeV 1+ carbon state, which decays to the 0+ ground state with a width of 38 eV, is of great interest. Its total width is about 43.6 eV and most of the width is ground state decay. However, exciting this state requires an electron beam with energies significantly above the approximate limit of 10 MeV specified above to limit the production of radioactivity and neutrons. Thus, the detection of carbon via this state, while attractive because of the very strong scattering, would involve additional complication and expense.

There are numerous states of the isotopes chlorine 35 and chlorine 37 that are of interest, resulting in photons with energies up to about 6 MeV with radiative widths in the range of the previous considerations. Thus, chlorine abundances can be determined as easily as those of oxygen, nitrogen, and carbon.

Many other elements have states of the appropriate energy and radiative widths. Therefore, the present invention is general in its usefulness. The method of the present invention can be used to detect almost any element of interest in a target. In addition to the explosives detection embodiment here, apparatus according to the present invention could be used in many industrial and commercial applications.

An important consideration for the estimation of count rates is the number of photons that are found within the width of the resonance in the bremsstrahlung spectrum. For a 10 MeV electron accelerator producing 10 $\mu$A of electrons, the bremsstrahlung spectrum can have about $10^6$ photons per eV at 7 MeV. Thus, for a state that is about 1/10 eV wide, about $10^5$ photons will lie within the range of the resonance and will be absorbed from the beam and re-emitted over all angles with very roughly an isotropic distribution. If 1/10 of the sphere is subtended with detectors that are 10% efficient, the counting rate will be about 1000 per second.

In this example, it was assumed that all the resonant photons are absorbed by the target 26. This is roughly correct for a small amount of material because of the large cross sections when thermal motion is neglected. With thermal motion there are always more photons available to scatter and thus the counting rates could be larger. However, the exact result depends on the geometry and thickness of the explosive material.

It is important to compare the signal with the expected background. In the preferred embodiments, the signal is a set of photo lines with energies of about 3-8 MeV. The background comes from the scattering of photons out of the beam by atomic processes. The major process is Compton scattering. Fortunately, if detectors are placed at scattering angles larger than 90 degrees to the bremsstrahlung beam, these Compton scattered photons will have energies below 0.5 MeV. The greater the angle past 90 degrees, the lower the energies of the Compton scattered photons, to a limit of 0.25 MeV for backscatter at 180 degrees. Pair production will also provide secondary bremsstrahlung that is predominantly forward peaked, as well as 0.5 MeV photons from $e^+e^-$ annihilation. There are coherent processes like Rayleigh scattering, but these should be very small at back angles, in particular for energies of a few MeV and above. Thus, there is no background in the energy region above 0.5 MeV except from multiple scattering processes and pile-up in the counters.

In order to minimize the effects of Compton scattering and maximize the signal-to-noise ration, the detecting apparatus 30 should be placed at an angle $\phi$ with respect to the bremsstrahlung beam 16 of considerably more than 90 degrees. An angle approaching 150 degrees is strongly preferred to make the signal stand out sufficiently from the noise of multiple processes.

There are many ways to arrange individual detectors 32 within a detecting apparatus 30. A preferred geometry is an annular array of detectors positioned to collect photons scattered back from the target at an angle $\phi$ of about 150 degrees. This is the embodiment illustrated in FIG. 1 where the detecting apparatus 30 is shown in cross-section. Of course, the array need not form a complete annulus around the path of the bremsstrahlung beam. For some embodiments, a vertical bank of detectors, one on each side of the bremsstrahlung beam 16, is preferred.

There are a variety of suitable detectors 32 that can be used in the detecting apparatus 30. In one embodiment, the detectors are intrinsic germanium ionization chambers where charge detectors pick up the electrical signal. In another embodiment, the detectors are scintillators such as NaI and BGO. The light emitted by these scintillators in response to incident photons can be converted to an electrical signal using a photo multiplier tube. This can be almost 100% efficient, leading to higher counting rates in the above example. It is important to recognize that the circuitry of the detecting apparatus must accommodate high counting rates and reduce pile-up.

The filter 34 is preferably placed in front of the detectors 32 to filter out low energy photons while passing the high energy photons of interest. A suitable material for this filter is a material with a low Z somewhere between that of carbon and iron. A high Z shield 36 is preferably placed around all but the face of the detector apparatus to absorb photons incident on the back and sides of the apparatus. Lead, bismuth, and iron are appropriate materials for this purpose. It may be necessary to include a shield 38 of hydrogenous material loaded with boron or lithium around the detectors to shield against neutrons generated in the luggage and beam dump. The high Z shadow shield 40 is preferably placed in the path between the aperture and the detectors to absorb all high-energy photon scattered from the aperture in the direction of the detectors. Lead is a suitable material for this purpose. The function of the shadow shield 40 could be performed by a heavy section of the shield 36.

The beam 16 passing through the target 26 will be attenuated by a relatively small amount. This beam must be absorbed in a beam dump 42 designed to absorb substantially all of the energy. A suitable beam dump for 10 MeV may be a layer 52 of a hydrogenous material containing boron or lithium, a layer 54 of carbon, and a layer 56 of iron in a very deep cavity formed in a shield 58 of lead or iron, for example, to shield the sides and the detectors from back-streaming low energy photons. A layer 60 of a hydrogenous material containing boron or lithium preferably surrounds the outside of this shield. The depth of this cavity, the beam dimensions, the directive collimation of the detectors, and the exact location of the detectors are related parameters that must be made compatible so as to not allow back-scattered photons from the beam dump to enter the detectors. Additional shadow shields may be set up to help meet this goal.

Imaging can be achieved in a variety of ways with the technique of the present invention. The luggage can be scanned with the beam by moving the bremsstrahlung-generating apparatus 5, the target 26, or simply the aperture 22. The electron beam can also be deflected by a magnet to sweep the bremsstrahlung beam direction. Preferred beam geometries are spots and stripes.

For example, if the beam 16 is collimated using a small square aperture to an average angle of $\Omega \approx 1/20$ radians (about 3 degrees), the spot 1 meter from the aperture will be about 10 cm $\times$ 10 cm, an excellent size for imaging the contents of a piece of luggage. If each measurement takes about $\frac{1}{4}$ second, an entire suitcase could be scanned in several seconds.

If the beam 16 is collimated using a vertical slit aperture to produce a thin stripe of 10 cm width at the point of incidence with a piece of luggage, a 60 cm long suitcase could be scanned in a few seconds as the suitcase moves on a conveyor belt. Alternatively, the beam 16 could be collimated into a spot swept vertically by an adjustable collimator or by magnetic deflection of the beam. Even if the collimation is in the form of a vertical stripe, the central intensity remains the highest, reflecting the natural collimation, and magnetic deflection of the beam will be useful for imaging.

Figure 2:
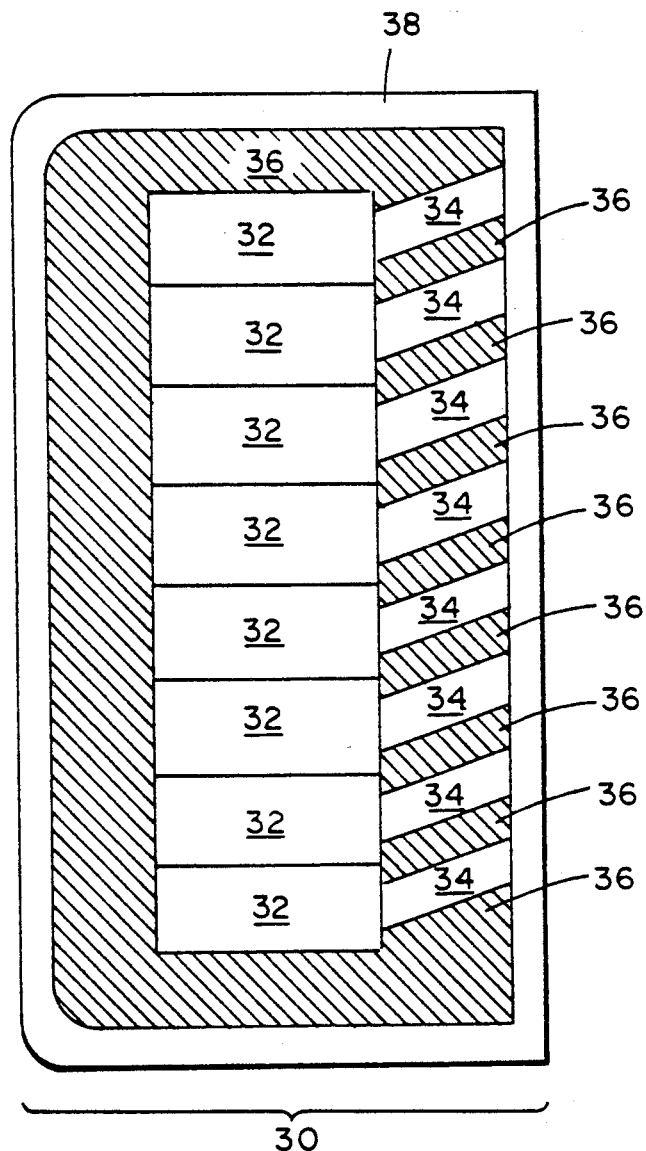
FIG. 2 is a schematic drawing of one embodiment of a detector array adapted for directional detection.

In another technique, a large portion of the suitcase is flooded with bremsstrahlung radiation by using a large aperture, and the detectors 32 are adapted to be direction-specific, as illustrated in FIG. 2. In this embodiment, part of the filter 34 covering the faces of the individual detectors 32 is replaced with high Z shielding 36. A column of low Z filter 34 remains for each individual detector. In this way, each detector can be designed to only detect photons scattered from a small specific region of the suitcase in a particular direction. An array of such detectors can easily be designed to image the entire suitcase to a desired degree of resolution.

A combination of the above imaging techniques results in a further embodiment of the present invention. For example, a thin slit aperture could be used to radiate thin vertical strips of the suitcase as the suitcase moves on a conveyor belt. The width of the strip will determine the horizontal resolution of the imaging. The vertical resolution could be increased by using directional detectors. Such a method would result in fast measurements at a high resolution.

Use of a rapidly adjustable collimating aperture 22 results in further embodiments with important advantages. For example, a piece of luggage could first be flooded with bremsstrahlung radiation in an effort to detect explosives in the form of thin sheets and/or to obtain an initial estimate of the abundances of various elements in its contents. The aperture could then be stopped down to image the suitcase in an effort to detect more localized explosive materials.

Another mode of operation is possible with the apparatus of the present invention. With a second bank of detectors located behind the target 26 to detect photons transmitted through the target, the intensity of photons absorbed in the target can be monitored. In this way, a very precise image of the transmission density of the target can be constructed. Such an image will identify specific areas of high material density in the target which would be a further aid in detecting explosive materials. Similar density imaging could be achieved by detecting the low energy back-scatter from the target.

Figure 4:
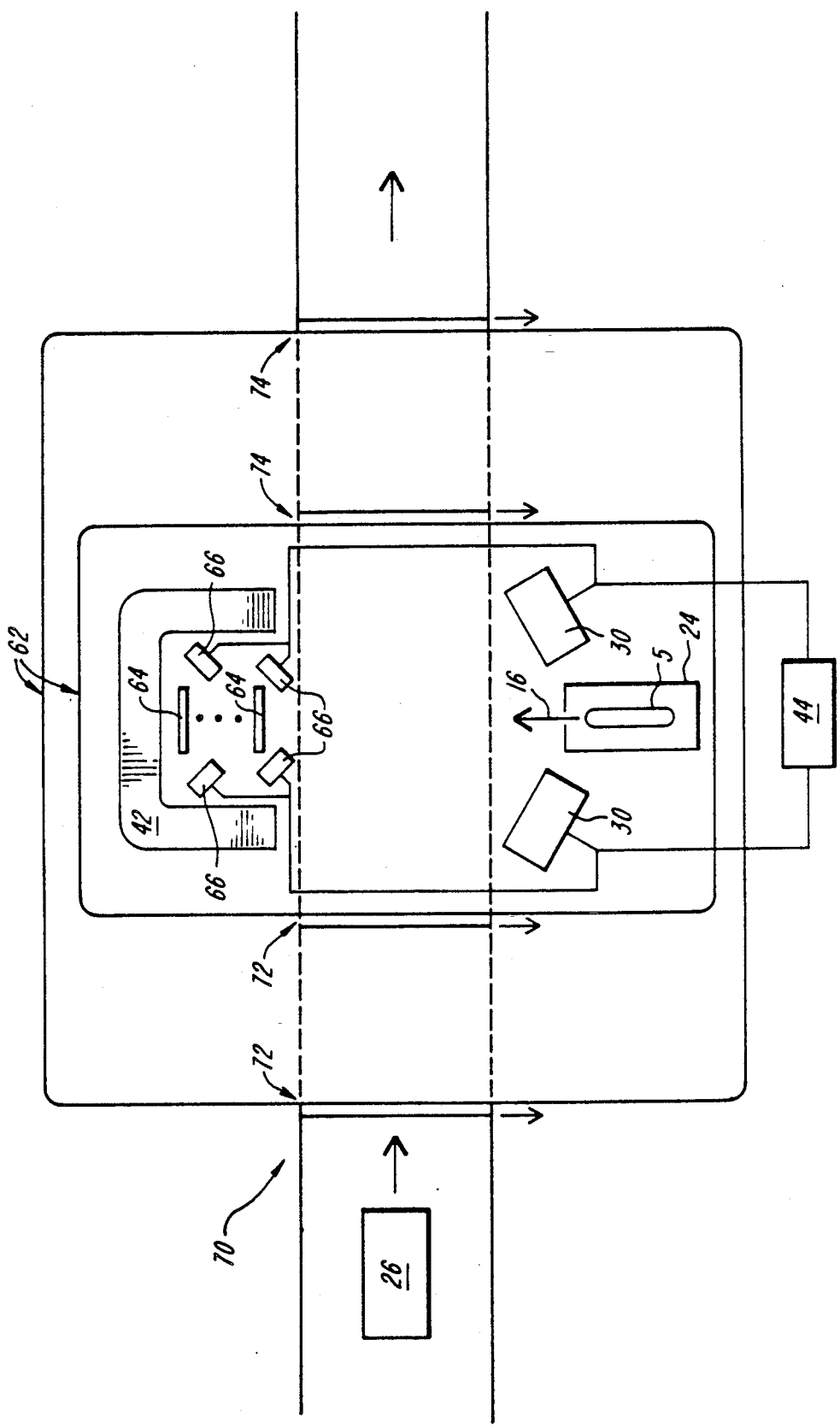
FIG. 4 is a schematic drawing of apparatus for conveying suitcases through the explosives detector.

Shielding 62 is required to protect the public from photons and neutrons generated by the explosives detection device. This shielding should enclose the device, while allowing a target to be quickly and conveniently moved into and out of the device. For example, as illustrated in FIG. 4, if the targets are suitcases on a conveyor belt 70, two sets of double doors 72 and 74, one set on each side of the device, would permit the entry and exit of the suitcases. This method is used in other explosives detection devices. Since the electron accelerator can be rapidly turned off and on, additional safety is provided by switching the accelerator off while targets are entering and/or exiting the device.

The fact that the electron accelerator can be rapidly switched on and off can be used to other advantages. For example, when the target is a large container, ranging could be achieved by making pulses of bremsstrahlung radiation incident on the target and measuring the delay of the photons scattered to the detectors. In this way, the depth of an explosive material into the container could be approximated. Pulses of less than a nanosecond in width are possible. The beam from an accelerator is often bunched, or can be made to be bunched, in subnanosecond intervals.

The computing apparatus 44 is adapted to analyze the data obtained by the detecting apparatus 30. As with other explosives detecting devices, profiles of elements, such as nitrogen and oxygen, as they appear in "normal" suitcases are preferably either modelled or experimentally determined. A suitcase which deviates significantly from these profiles would be considered "suspicious". The computing apparatus can be easily adapted to compare data to stored profiles. If the profiles are rigorously determined, a high probability of explosives detection accompanied by a low rate of false alarms will be achieved.

Figure 3:
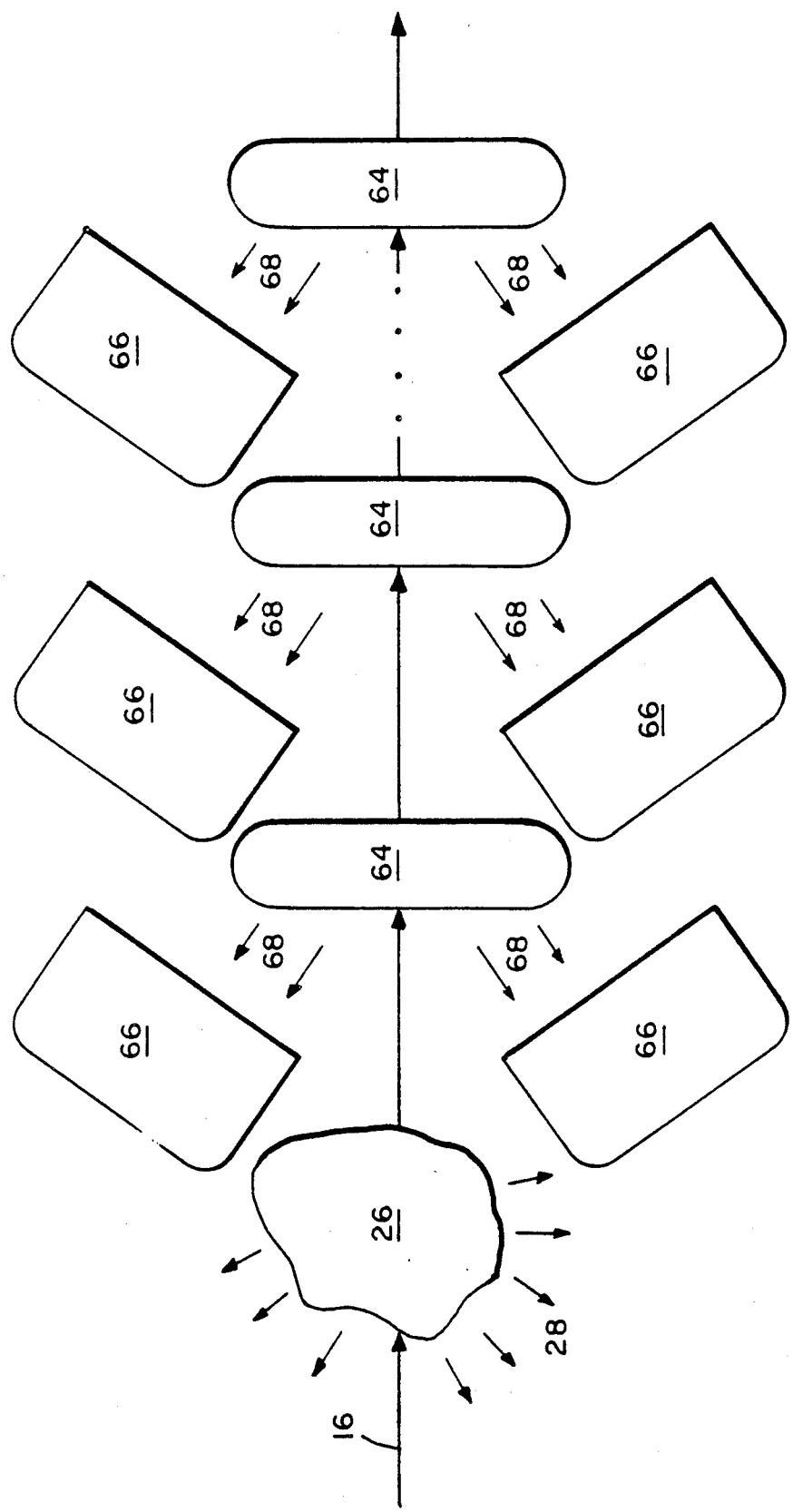
FIG. 3 is a schematic diagram of one embodiment of an alternate detecting scheme of the present invention.

An alternate detecting scheme according to the present invention is illustrated in one embodiment in FIG. 3. For simplicity, only those elements relevant to the detecting scheme are shown. As shown, the bremsstrahlung beam 16 is made incident on the target 26. As the beam 16 passes through the target 26, photons will be resonantly absorbed by the nuclei of the target. The energies of the absorbed photons correspond to the spacings between the quantized energy states of each nuclear species in the target. For these specific energies, the transmitted beam will be depleted of photons. For example, if the target contains nitrogen, photons of energies corresponding to nitrogen will be selectively absorbed. The amount of photons absorbed depends on the quantity of nitrogen in the target. Thus, the intensities of the photons of specific energies transmitted through the target contains information about the nuclear composition of the target. This information is exploited in the embodiment shown in FIG. 3. As shown, a series of reference resonance scatterers 64 are arranged behind the target 26. Each reference scatterer is composed of one or more of the elements that the explosives detecting device is to detect. A series of detecting apparatuses 66 is adapted to capture, measure, count, and record the photons 68 resonantly scattered from each of the reference scatterers 64. For example, in a simple embodiment, two reference scatterers are provided, one of nitrogen, the other of oxygen. A detecting apparatus is adapted to detect photons resonantly scattered from the nuclei in the nitrogen scatterer and another detecting apparatus is adapted to detect photons resonantly scattered from the nuclei in the oxygen scatterer.

This detecting scheme operates as follows. If no target 26 is placed in the path of the beam 16, the beam will directly strike the first of the reference resonance scatterers 64. The detecting apparatus associated with the first reference scatterer will detect a large amount of photons corresponding to the nuclear species of the first reference scatterer. If a target 26 with a relatively small amount of the nuclear species of the first reference scatterer is placed in the path of the beam, this strong signal at the first detecting apparatus will be diminished by only a relatively small amount. If however, a target 26 with a relatively large amount of the nuclear species of the first reference scatterer is placed in the path of the beam, this signal will be diminished considerably, due to the resonant absorption of the photons of energies corresponding to the nuclear species of interest in the target 26. Thus, an abundance of a nuclear species of interest in a target 26 will be detected as a decrease in the signal from the detecting apparatus associated with a reference scatterer composed substantially of that nuclear species. Photons of energies not corresponding to the nuclear species of which a reference scatterer is substantially composed will be attenuated by only a relatively small amount. Thus, the method of detecting the nuclear species of the first reference scatterer extends to the each subsequent reference scatterer. An advantage of this detecting scheme is that if the energies corresponding to two or more nuclear species of interest are very close, the detecting apparatus of the embodiment of FIG. 1 may have difficulty distinguishing the contributions from the two or more nuclear species. However, in the embodiment of FIG. 3, the energies corresponding to each nuclear species are detected separately, this ambiguity is diminished considerably, and the ability of the detecting apparatus to resolve closely spaced photon energies is no longer very important. When the energies corresponding to two or more nuclear species do not interfere, a single reference scatterer can be composed of a combination of the species.

The requirements for each detecting apparatus 66 in the series are similar to those described for the detecting apparatus 30 of the embodiment of FIG. 1. Thus, each detecting apparatus preferably includes an array of detectors, and shielding and filtering means as indicated by elements 32, 34, 36, and 38 of FIG. 1. The various detecting apparatus configurations discussed above are applicable to the embodiment of FIG. 3. In order to minimize the effects of Compton scattering and maximize the signal-to-noise ratio, the detecting apparatuses 66 should be placed at an angle $\phi$ with respect to the bremsstrahlung beam 16 of considerably more than 90 degrees. An angle approaching 150 degrees is strongly preferred to make the signal stand out sufficiently from the noise of multiple processes. It must be noted that backscatter from any of the reference scatterers 64 and the detecting apparatuses 66 must be taken into account when positioning the reference scatterers and detecting apparatuses. Appropriate shielding may be required to isolate the detectors from backscatter from reference resonance scatterers with which they are not associated. The adaptions for direction detection pictured in FIG. 2 are also appropriate for this alternate detecting scheme. Similarly, the imaging methods described above can be employed in this scheme. A further imaging scheme appropriate to this embodiment employs reference resonance scatterers which are small with respect to the dimensions of the target 26. Imaging can then be achieved while the target 26 is flooded with bremsstrahlung radiation by moving the scatterers to scan the extent of the target.

All elements not shown in FIG. 3, such as the bremsstrahlung source, the beam dump, the shielding, and the computing apparatus are similar to that shown in FIG. 1. In this alternate detecting scheme, the computing apparatus is adapted to compare the intensities of photon energy levels detected by the detecting apparatuses 66 to reference values. Clearly an appropriate set of reference values are the intensities measured when the target 26 is not placed in the path of the bremsstrahlung beam. In that way, the decreases in intensity measured when the target is placed in the path of the beam can be directly related to the composition of the target. Alternatively the reference values may be determined from profiles of "normal" targets, as discussed above in relation to the first detecting scheme.

A further detecting scheme involves a combination of the detecting schemes illustrated in FIG. 1 and FIG. 3. It may be advantageous to detect both the photons resonantly scattered directly from the target 26 and those resonantly scattered from the reference scatters 64. The two schemes are completely compatible.

It is recognized that variations and modifications of the present invention will occur to those skilled in the art, and it is intended that all such variations and modifications be within the scope of the claims.

What is claimed is:

1. A method for detecting explosive materials in a target, the explosive materials containing characteristically large or small amounts of one or more nuclear species of interest, comprising:
   resonantly exciting nuclei of the target with a beam of bremsstrahlung radiation,
   resonantly exciting nuclei of one or more reference scatterers with the beam of bremsstrahlung radiation transmitted through the target, each said reference scatterer comprising one or more of the nuclear species of interest,
   measuring the intensity of photons at energies of interest scattered from each said reference scatterer in a direction or directions, said energies of interest for each reference scatterer corresponding to the spacings between the quantized energy states of the nuclear species of interest of which the reference scatterer is comprised, and
   estimating the abundance of each nuclear species of interest in the target from the measured intensity of photons scattered from the reference scatterer or scatterers comprising the nuclear species.

2. A method for detecting explosive materials in a target, the explosive materials containing characteristically large or small amounts of one or more nuclear species of interest, comprising:
   resonantly exciting the nuclei of the target with bremsstrahlung radiation,
   resonantly exciting nuclei of one or more reference scatterers with the beam of bremsstrahlung radiation transmitted through the target, each said reference scatterer comprising one or more of the nuclear species of interest,
   measuring the intensity of photons at energies of interest scattered from each said reference scatterer in a direction or directions, said energies of interest for each reference scatterer corresponding to the spacings between the quantized energy states of the nuclear species of interest of which the reference scatterer is comprised, and comparing the intensities of photons at energies of interest to profiles of intensities for comparable targets not containing explosives and/or to comparable targets containing explosives to determine if the target is likely to contain explosives.

3. A method for detecting one or more nuclear species of interest in a target comprising:

resonantly exciting the nuclei of the target with bremsstrahlung radiation, resonantly exciting nuclei of one or more reference scatterers with the beam of bremsstrahlung radiation transmitted through the target, each said reference scatterer comprising one or more of the nuclear species of interest, and detecting photons at energies of interest scattered from each said reference scatterer in a direction or directions, said energies of interest for each reference scatterer corresponding to the spacings between the quantized energy states of the nuclear species of interest of which the reference scatterer is comprised, whereby the detection of an insufficient intensity of photons corresponding to the spacings between the quantized energy states of a nuclear species of interest indicates the presence of at least a threshold amount of the nuclear species in the target.

4. A method for detecting one or more nuclear species in a target comprising:

resonantly exciting the nuclei of the target with bremsstrahlung radiation, resonantly exciting nuclei of one or more reference scatterers with the beam of bremsstrahlung radiation transmitted through the target, each said reference scatterer comprising one or more of the nuclear species of interest, measuring photons at energies of interest scattered from each said reference scatterer in a direction or directions, said energies of interest for each reference scatterer corresponding to the spacings between the quantized energy states of the nuclear species of interest of which said reference scatterer is comprised, and estimating the abundance of each nuclear species of interest in the target from the measured intensity of photons scattered from the reference scatterer or scatterers comprising the nuclear species.

5. The method of claim 1 further comprising:

measuring the intensity of photons at energies of interest scattered from the target in a direction or directions, said energies of interest corresponding to the spacings between the quantized energy states of nuclear species of interest, said nuclear species of interest being the same as of different from the nuclear species referred to in claim 1, and estimating the abundance of nuclear species of interest in the target from the measured intensity of photons scattered from the target which correspond to nuclear species of interest.

6. The method of claim 2 further comprising:

measuring the intensities of photons at energies of interest scattered from the target in a direction or directions, said energies of interest corresponding to the spacings between the quantized energy states of nuclear species of interest, said nuclear species of interest being the same as or different from the nuclear species referred to in claim 2, and comparing the intensities of the photons at energies of interest scattered from the target to profiles of intensities for comparable targets not containing explosives and/or to comparable targets containing explosives to determine if the target is likely to contain explosives.

7. The method of claim 3 further comprising:

detecting photons at energies of interest scattered from the target in a direction or directions, said energies of interest corresponding to the spacings between the quantized energy states of nuclear species of interest, said nuclear species of interest being the same or different nuclear species referred to in claim 3, whereby the detection of a sufficient intensity of photons scattered from the target corresponding to the spacings between the quantized energy states of a nuclear species of interest indicates the presence of at least a threshold amount of that nuclear species in the target.

8. The method of claim 4 further comprising:

detecting photons at energies of interest scattered from the target in a direction or directions, said energies of interest corresponding to the spacings between the quantized energy states of nuclear species of interest, said nuclear species of interest being the same or different nuclear species referred to in claim 4, and estimating the abundance of nuclear species of interest in the target from the measured intensity of photons scattered from the target which corresponds to nuclear species of interest.

9. The method of claims 1, 2, 3, 4, 5, 6, 7, or 8 wherein the target is imaged by collimating said radiation to a beam, the beam cross-section having at least one dimension which is small with respect to the target, and scanning said beam over the extent of the target by moving the beam, the target, or both.

10. The method of claims 1, 2, 3, 4, 5, 6, 7, or 8 wherein the target is imaged by collimating said radiation to a beam having a cross-section which is on the order of the size of the target, flooding the target with said radiation, and employing directional detection of the scattered photons.

11. The method of claims 1, 2, 3, 4, 5, 6, 7, or 8 wherein the target is imaged by a combination of the methods of:

collimating said radiation to a beam, the beam cross-section having at least one dimension which is small with respect to the target, and scanning said beam of over the extent of the target by moving the beam, the target, or both, and employing directional detection of the scattered photons.

12. The method of claims 1, 2, 3, 4, 5, 6, 7, or 8 wherein the target is imaged by employing reference scatterers which are small with respect to the dimensions of the target, by collimating said radiation to a beam having a cross-section which is on the order of the size of the target, flooding the target with said radiation, and moving said reference scatterers in order to scan the target.

13. The method of claims 1, 2, 3, 4, 5, 6, 7, or 8 wherein the target is examined a plurality of times in succession, each examination comprising collimating said radiation to a beam of a different cross-section.

14. The method of claims 1, 2, 3, 4, 5, 6, 7, or 8 further comprising imaging the density of the target by detecting the photons transmitted through the target.

15. The method of claims 1, 2, 3, 4, 5, 6, 7, or 8 further comprising imaging the density of the target by detecting the photons back-scattered from the target.

16. The method of claims 1, 2, 3, 4, 5, 6, 7, or 8 further comprising ranging, wherein the location of a nuclear species of interest in a target is approximately by employing a pulsed source of bremsstrahlung radiation and by measuring the delay of photons scattered from the target.

17. A device for detecting explosive materials in a target comprising:
   a shielded source of bremsstrahlung radiation,
   means for making the bremsstrahlung radiation incident on the target,
   one or more reference resonance scatterers positioned such that bremsstrahlung radiation transmitted through the target will be incident on said reference scatterers,
   one or more detecting apparatuses each comprising an array of individual detectors for capturing, measuring, counting, and recording the energies of photons scattered from said reference scatterers, and
   computing apparatus for accepting data from said detecting apparatuses, and for using this data to determine if the target is likely to contain explosive materials.

18. A device for detecting one or more nuclear species in a target comprising:
   a shielded source of bremsstrahlung radiation,
   means for making the bremsstrahlung radiation incident on the target, and
   one or more reference resonance scatterers positioned such that bremsstrahlung radiation transmitted through the target will be incident on said reference scatterers,
   one or more detecting apparatuses each comprising an array of individual detectors for capturing, measuring, counting, and recording the energies of photons scattered from said reference scatterers.

19. The device of claim 17 further comprising detecting apparatus comprising an array of individual detectors for capturing, measuring, counting, and recording the energies of photons scattered from the target, said computing apparatus adapted to accept data from said detecting apparatus, and for using this data to determine if the target is likely to contain explosive materials.

20. The device of claim 18 further comprising detecting apparatus comprising an array of individual detectors adapted to capture, measure, count, and record the energies of photons scattered from the target.

21. The device of claims 17, 18, 19, or 20 wherein said source of bremsstrahlung radiation comprises an electron accelerator producing electrons incident on a bremsstrahlung target.

22. The device of claim 21 wherein said source of bremsstrahlung radiation further comprises a beam stopper following said bremsstrahlung target for absorbing substantially all electrons exiting said bremsstrahlung target.

23. The device of claims 17, 18, 19, or 20 wherein said source of bremsstrahlung radiation comprises an aperture for collimating said bremsstrahlung radiation to a beam of a desired shape and angular spread.

24. The device of claims 17, 18, 19, or 20 wherein said source of bremsstrahlung radiation comprises a filter for absorbing the low energy photons of the bremsstrahlung spectrum preferentially over the high energy photons.

25. The device of claims 17 or 19 wherein said detecting apparatus counts scattered photons of energy about 4.92 MeV to detect nitrogen in the target.

26. The device of claims 17 or 19 wherein said detecting apparatus counts scattered photons of energy about 7.03 MeV to detect nitrogen in the target.

27. The device of claims 17 or 19 wherein said detecting apparatus counts scattered photons of energy about 6.92 MeV to detect oxygen in the target.

28. The device of claims 17 or 19 wherein said detecting apparatus counts scattered photons of energy about 7.12 MeV to detect oxygen in the target.

29. The device of claims 17 or 19 wherein said detecting apparatus counts scattered photons of energy about 4.44 MeV to detect carbon in the target.

30. The device of claims 17 or 19 wherein at least one of said reference scatterers comprises nitrogen.

31. The device of claims 17 or 19 wherein at least one of said reference scatterers comprises oxygen.

32. The device of claims 17 or 19 wherein at least one of said reference scatterers comprises carbon.

33. The device of claims 17, 18, 19, or 20 wherein said detecting apparatuses detect photons scattered at an angle of greater than 90 degrees from the direction of said bremsstrahlung beam.

34. The device of claims 17, 18, 19, or 20 wherein said detecting apparatuses detect photons scattered at an angle of approximately 150 degrees from the direction of said bremsstrahlung beam.

35. The device of claims 17, 18, 19, or 20 wherein said individual detectors are intrinsic germanium ionization chambers.

36. The device of claims 17, 18, 19, or 20 wherein said individual detectors are scintillators.

37. The device of claims 17, 18, 19, or 20 further comprising a filter in front of said individual detectors to absorb the low energy scattered photons preferentially over the high energy photons.

38. The device of claims 17 or 19 wherein said means for making said bremsstrahlung beam incident on the target is a conveyor belt which moves the target into position in front of the aperture.

39. The device of claims 17, 18, 19, or 20 further comprising means for making said individual detectors direction-specific.

40. The device of claim 39 wherein said means for making said individual detectors direction-specific comprises a thickness of a high atomic number shielding material over each individual detector with a column of said shielding material removed, the axis of said column pointing in a specific direction, whereby each individual detector will detect only photons scattered from a particular location in a particular direction.

41. The device of claim 17 or 19 wherein said computing apparatus compares the data from the detecting apparatuses to profiles of data stored in said computing apparatus, said profiles corresponding to comparable targets not containing explosives and/or to comparable targets containing explosives to determine if the target is likely to contain explosives.

42. The device of claim 17 or 19 wherein said computing apparatus compares the data from the detecting apparatuses to reference data corresponding to the signals received by the detecting apparatuses when the target is not placed in the path of the bremsstrahlung beam.

* * * * *

UNITED STATES PATENT AND TRADEMARK OFFICE
CERTIFICATE OF CORRECTION

PATENT NO. : 5,115,459  
DATED : May 19, 1992  
INVENTOR(S) : William Bertozzi

Page 1 of 2

It is certified that error appears in the above-indentified patent and that said Letters Patent is hereby corrected as shown below:

Column 2, line 24: delete "strip" and insert therefor -- stripe --;

Column 3, line 42: after "that" and before "radioactivity" insert -- substantial --;

Column 3, line 67: delete "target" and insert therefor -- present --;

Column 6, line 43: delete "1$^-$" and insert therefor -- 1$^+$ --;

Column 6, line 49: delete "0$^{30}$" and insert therefor -- 0$^+$ --;

Column 7, line 30: after "embodiment" and before "here" insert -- described --;

Column 7, line 56: delete "photo" and insert therefor -- photon --;

Column 8, line 7: delete "ration" and insert therefor -- ratio --;

Column 9, line 47 delete "strips" and insert therefor -- stripes --;

Column 9, line 48, delete "strip" and insert therefor -- stripe --;

Column 12, line 27: delete "scatters" and insert therefor -- scatterers --;

Column 14, line 55: delete "of";

Column 15, line 11: delete "approximately" and insert therefor -- approximated --; and

UNITED STATES PATENT AND TRADEMARK OFFICE
CERTIFICATE OF CORRECTION

PATENT NO. : 5,115,459
DATED : May 19, 1992
INVENTOR(S) : William Bertozzi

It is certified that error appears in the above-indentified patent and that said Letters Patent is hereby corrected as shown below:

Column 15, line 48: delete "adapted to accept" and insert therefor -- for accepting --.

Signed and Sealed this

First Day of March, 1994

Attest:

BRUCE LEHMAN

Attesting Officer

Commissioner of Patents and Trademarks